United States Patent
Toppare et al.

(10) Patent No.: US 8,324,400 B2
(45) Date of Patent: Dec. 4, 2012

(54) BENZOTRIAZOLE CONTAINING DONOR-ACCEPTOR TYPE POLYMER AS A MULTI-PURPOSE MATERIAL

(76) Inventors: Levent Kamil Toppare, Ankara (TR); Abidin Balan, Ankara (TR); Derya Baran, Ankara (TR)

( * ) Notice: Subject to any disclaimer, the term of this patent is extended or adjusted under 35 U.S.C. 154(b) by 0 days.

(21) Appl. No.: 13/325,532

(22) Filed: Dec. 14, 2011

(65) Prior Publication Data
US 2012/0083583 A1 Apr. 5, 2012

Related U.S. Application Data

(60) Division of application No. 12/749,894, filed on Mar. 30, 2010, now abandoned, which is a continuation-in-part of application No. PCT/TR2009/000045, filed on Mar. 30, 2009.

(51) Int. Cl.
*C07D 249/16* (2006.01)
(52) U.S. Cl. ........ 548/257; 548/260; 528/423; 528/380; 528/377; 528/370

(58) Field of Classification Search .................. 528/370, 528/380, 373, 377, 423
See application file for complete search history.

(56) References Cited

U.S. PATENT DOCUMENTS
2006/0083945 A1* 4/2006 Morishita et al. ............. 428/690

OTHER PUBLICATIONS

International Search Report for PCT/TR2009/000045.
International Preliminary Report on Patentability PCT/TR2009/000045.
Reply to International Search Report for PCT/TR2009/000045.

* cited by examiner

*Primary Examiner* — Shane Fang
(74) *Attorney, Agent, or Firm* — Donald J. Ranft; Collen IP (57) ABSTRACT

This invention is about a material which provides to observe all colors necessary for display technologies in a very small potential range. The material is a derivative of benzotriazole containing donor acceptor type conducting polymer which is soluble, fluorescent and can be used in LEDs, solar cells, electrochromic devices, smart windows and many other technologies.

1 Claim, 13 Drawing Sheets

BENZOTRIAZOLE CONTAINING DONOR-ACCEPTOR TYPE POLYMER AS A MULTI-PURPOSE MATERIAL

This application claims priority to and is a divisional of U.S. patent application Ser. No. 12/749,894 filed Mar. 30, 2010 which is incorporated herein by reference. Patent application Ser. No. 12/749,894 is a continuation of PCT application PCT/TR2009/000045 filed on Mar. 30, 2009.

FIELD OF INVENTION

This invention is about a material which provides to observe all colors necessary for display technologies in a very small potential range. The material is a derivative of benzotriazole containing donor acceptor type conducting polymer which is soluble, fluorescent and can be used in LEDs, solar cells, electrochromic devices, smart windows and many other technologies.

PRIOR ART

The list of the references in the prior art are below:
[1] H. Shirakawa, E. J. Louis, A. G. Macdiamid, C. K. Chinag, A. J. Heeger, *Chem. Commun.* 1977, 16, 578-580.
[2] G. A. Niklasson, C. G. Granqvist, *J. Mater. Chem.* 2007, 17, 127-156.
[3] J. H. Burroughes, D. D. C. Bradley, A. R. Brown, R. N. Marks, K. Mackay, R. H. Friend, P. L. Burns, A. B. Holmes, *Nature* 1990, 347, 539-541.
[4] H. Hoppe, M. Niggemann, C. Winder, J. Kraut, R. Hiesgen, A. Hinsch. D. Meissner, N. S. Sariciftci, *Adv. Funct. Mater.* 2004, 14, 1005-1011.
[5] D. T. McQuade, A. E. Pullen, T. M. Swager, *Chem. Rev.* 2000, 100, 2537-2574.
[6] H. Koezuka, A. Tsumura *Synthetic Metals* 1989, 28, 1-2.
[7] P. M. S. Monk, R. J. Mortimer, D. R. Rosseinsky, *Electrochromism: Fundamentals and Applications*, VCH, Weinheim, Germany, 1995, 3-5.
[8] A. Kumar, D. M. Welsh, M. C. Morvant, F. Piroux, K. A. Abboud, J. R. Reynolds, *Chem. Mater.* 1998, 10, 896-902.
[9] S. A. Sapp, G. A. Sotzing, J. R. Reynolds, *Chem. Mater.* 1998, 10, 2101-2108.
[10] G. Sonmez, H. B. Sonmez, C. K. F. Shen, R. W. Jost, Y. Rubin, F. Wudl, *Macromolecules* 2005, 38, 669-675.
[11] I. Schwendeman, R. Hickman, G. Sonmez, P. Schottland, K. Zong, D. Welsh, J. R. Reynolds, *Chem. Mater.* 2002, 14, 3118-3122.
[12] a) C. Pozo-Gonzalo, M. Salsamendi, J. A. Pomposo, H. J. Grande, E. Y. Schmidt, Y. Y. Rusakov, B. A. Trofimov, *Macromolecules* 2008, 41, 6886-6894 b) E. Yildiz, P. Camurlu, C. Tanyeli, I. Akhmedov, L. Toppare, *J. Electroanal. Chem.* 2008, 612, 247-256. c) C. L. Gaupp, J. R. Reynolds, *Macromolecules* 2003, 36, 6305-6315.
[13] Y. A. Udum, A. Durmus, G. E. Gunbas, L. Toppare, *Org. Electron.* 2008, 9, 501-506.
[14] B. C. Thompson, Y. Kim, T. D. McCarley, J. R. Reynolds, *J. Am. Chem. Soc.* 2006, 128, 12714-12725.
[15] a) A. Durmus, G. E. Gunbas, P. Camurlu, L. Toppare, *Chem. Commun.* 2007, 31, 3246-3248. b) G. E. Gunbas, A. Durmus, L. Toppare, *Adv. Mater.* 2008, 20, 691-695. c) G. E. Gunbas, A. Durmus, L. Toppare, *Adv. Funct. Mater.* 2008, 18, 2026-2030.
[16] D. M. Leeuw, M. M. Simenon, A. R. Brown, R. E. F. Einerhand, *Synth. Met.* 1997, 87, 53-59.
[17] a) K. Harada, A. G. Werner, M. Pfeiffer, C. J. Bloom, C. M. Elliott, K. Leo, *Phys. Rev. Let.* 2005, 94, 1-4. b) J. W. Ma, W. Xu, X. Y. Jiang, Z. L. Zhang, *Synt. Met.* 2008, 158, 810-814. c) M. A. Khan, W. Xu, K. Haq, Y Bai, F. Wei, X. Y. Jiang, Z. L. Zhang, W. Q. Zhu, *J. Phys. D: Appl. Phys.* 2007, 40, 6535-6540.
[18]a) A. Balan, G. Gunbas, A. Durmus, L. Toppare, *Chem. Mater.* 2008, 20, 7510-7513.
[18]b) G. A. Cetin, A. Balan, A. Durmus, G. Gunbas, *Org. Electron.* 2009, 10, 34-41
[19] a) F. Ozyurt, E. G. Gunbas, A. Durmus, L. Toppare, *Org. Electron.* 2008, 9296-302. b) G. A. Sotzing, J. L. Reddinger, A. R. Katritzky, J. Soloducho, R. Musgrave, J. R. Reynolds, P. J. Steel, *Chem. Mater.*, 1997, 9, 1578-1587. c) P. R. Somani, S. Radhakrishnan, *Mat. Chem. Phys.* 2002, 77, 117-133. d) M. Kaneko, *Makromol. Chem. Rapid Commun.* 1987, 8, 179-180. e) J. L. Reddinger, G. A. Sotzing, J. R. Reynolds, *Chem. Commun.* 1996, 1777-1778.
[20] P. M. Beaujuge, S. Ellinger, J. R. Reynolds, *Nature Mater.* 2008, 7, 795-799.
[21] G. Sonmez, C. K. F. Shen, Y. Rubin, F. Wudl, *Angew. Chem. Int. Ed.* 2004, 43, 1498-1502.
[22] C. J. DuBois, K. A. Abboud, J. R. Reynolds, *J. Phys. Chem.* 52004, 108, 8550-8557.
[23] C. J. DuBois, J. R. Reynolds, *Adv. Mater.* 2002, 14, 1844-1846.
[24] a) Y. Pang, X. Li, H. Ding, G. Shi, L. Jin, *Electrochim. Acta* 2007, 52, 6172-6177. b) C. H. Woo, B. C. Thompson, B. J. Kim, M. F. Toney, J. M. J. Frechet, *J. Am. Chem. Soc.* 2008, 130, 16324-16329.
[25] a) W. Ma, C. Yang, X. Gong, K. Lee, A. Heeger, *J. AdV. Funct. Mater.* 2005, 15, 1617-1622. b) S. Gunes, H. Neugebauer, N. S. Sariciftci, *Chem. Rev.* 2007, 107, 1324-1338.
[26] a) A. M. McDonagh, S. R. Bayly, D. J. Riley, M. D. Ward, J. A. McCleverty, M. A. Cowin, C. N. Morgan, R. Varrazza, R. V. Penty, I. H. White, *Chem. Mater.* 2000, 12, 2523-2524. b) H. Meng, D. Tucker, S. Chaffins, Y. Chen, R. Helgeson, B. Dunn, F. Wudl, *Adv. Mater.* 2003, 15, 146-149.
[27] G. Sonmez, H. B. Sonmez, *J. Mater. Chem.* 2006, 16, 2473-2477.
[28] G. Sonmez, *Chem. Commun.* 2005, 5251-5259.
[29] C. L. Gaupp, D. M. Welsh and J. R. Reynolds, *Macromol. Rapid. Commun.* 2002, 23, 885-889.
[30] G. Sonmez, H. B. Sonmez, lifton K. F. Shen, F. Wudl, *Adv. Mater* 2004, 16, 1905-1908.

Since the discovery of conducting polymers [1] they became a fundamental research subject both in academia and industry. They have been used as active materials in numerous industrial applications namely, electrochromics,[2] LEDs,[3] solar cells,[4] sensors[5] and field effective transistors.[6] There have been many different types and derivatives of conducting polymers were successfully prepared over the decades and their potential as advanced materials have been investigated for numerous applications. Studies in electrochromic devices mainly focused on inorganic materials namely, tungsten trioxide ($WO_3$) and iridium dioxide ($IrO_2$).[7] The use of conjugated polymers as active layers in electrochromic devices became more popular over the time due to their fast switching times,[8] high optical contrasts,[9] processibility,[10] and easy tuning of color via structure alternations.[11]

Another aspect that attracted the researchers towards the polymeric materials is; multicolors can be achieved with minor structural variations on the material. Multichromic polymers have become a major field of research due their potential use in many different applications like display systems and smart windows.[12]

One of the properties of conducting polymers is their great potential to be n-doped. However, the research on the n-doping characteristics of these materials resulted in a handful of materials exhibiting this unique property.[13-15] The n-doped semiconducting polymers will have a great impact since it will open the way for the fabrication of light emitting diodes, bipolar transistors, and polymeric analogue of silicon weld effective transistors.[16, 17]

In prior art, benzothiadiazole or quinoxaline containing donor-acceptor polymers led to the first neutral state green polymeric material with highly transmissive oxidized state[15].

Additionally, in the PCT application (PCT/TR2008/000035) filed by one of the applicants of this invention (Levent Kamil TOPPARE), having the title, UNIQUE PROCESSABLE GREEN POLYMER WITH A TRANSMISSIVE OXIDIZED STATE FOR REALIZATION OF COMMERICAL RGB BASED ELECTROCHROMIC DEVICE APPLICATIONS; "A method for synthesis of neutral state green polymer (PDOPEQ) is developed and this method was characterized by;
  a) obtaining 2,3-bis(3,4-bis(decyloxy)phenyl)-5,8-dibromoquinoxaline,
  b) obtaining tributyl (2,3-dihydrothieno[3,4-b][1,4]dioxin-5-yl)stannane
  c) using coupling to attach donor EDOT moieties to the acceptor quinoxaline unit to give the title compound (DOPEQ)

DOPEQ in satisfactory yields;
  d) obtaining neutral state green polymer (PDOPEQ) by using either electrochemical or chemical methods.

The polymers synthesized up to date mainly absorb/reflect blue and red colors in the reduced state. Conversely, to obtain a green colored polymer in the reduced state, one should have two absorption bands centered at the blue and red regions of the visible spectrum and moreover, these absorption bands should be manipulated in the same manner at applied potentials that have been disclosed.

These results have opened the way for utilization of electrochromic polymers in display devices. The remarkable behavior of donor-acceptor type polymers as active layers in electrochromic devices resulted in the synthesis of novel polymers containing alkylated benzotriazole as the acceptor unit. The donor-acceptor type molecules synthesized previously with benzotriazole using ethylenedioxythiophene and selenophene units resulted in polymers showing superior characteristics than donor units.[18a, 18b] These results led to synthesize novel molecules bearing benzotriazole unit as the acceptor and polymerizable electron-rich aromatic units as the donor.

AIMS OF THE INVENTION

In present invention,
Development of a conducting polymer which enables the transition between all colors especially red, green, blue, black and transparent colors required in display systems,
Obtaining a conducting polymer which is soluble in many different organic solvents,
Obtaining a conducting polymer which is both p and n-dopable,
Obtaining a conducting polymer which emits light,
Obtaining a conducting polymer which is applicable on both LEDs and the active surface of solar cells,
Obtaining a conducting polymer which has numerous area of use are aimed.

DESCRIPTION OF THE FIGURES

Scheme 1: Synthesis of 1, 2, 3, TBT, PI and PII.

FIG. S-1: Single scan cyclic voltammetry of PII on an ITO electrode at 100 mV s$^{-1}$ in 0.1M TBAPF$_6$/ACN.

FIG. S-2: Scan rate dependence of PII film on ITO, in TBAPF$_6$/ACN at: (a) 100, (b) 150, (c) 200, (d) 250 and (e) 300 mV s$^{-1}$ FIG. S-3: Electronic absorption spectra of PII film on ITO coated glass slide in monomer free, 0.1M TBAPF$_6$/ACN electrolyte-solvent couple at applied potentials (V). 1) p-doping (a) 0.850, (b) 0.875, (c) 0.900, (d) 0.950, (e) 1.00, (f) 1.05, (g) 1.10, (h) 1.15, (i) 1.20, (j) 1.25, (k) 1.30, (I) 1.35 and (m) 1.40V. 2) n-doping (a)−1.84, (b)−1.85, (c)−1.86, (d)−1.87, (e)−1.88.

FIG. S-4: Electrochromic switching: optical absorbance change monitored at 525, 750 and 1250 nm for PII in 0.1 M TBAPF$_6$/ACN while switching between its fully reduced and oxidized states.

FIG. S-5: Solution optical absorbance spectra of TBT, PI, PII in CHCl$_3$.

FIG. S-6: Chronoamperometry experiment for PI on ITO glass in 0.1 M TBAPF$_6$/ACN while switching between reduced and oxidized states. The first four cycles and the ones after the 1000$^{th}$ cycle are presented. Each interval on the x axes stands for 5 s.

DETAILED EXPLANATION OF THE INVENTION

The basic idea was to enhance the electrochromic characteristics of the homopolymer of the donor unit, poly- thiophene. The resulting polymer has shown tremendous advancement compare to polythiophene and revealed numerous and exciting new properties that have not been observed previously for any polymer.

The resulting polymer has six distinct colors, which is a very rare and unique property for homopolymers[19].

The polymer also was shown to be both p and n-dopable by cyclic voltammetry and spectroelectrochemistry experiments. The optical contrast and switching time of the polymer were greatly improved. In addition, the polymer is highly fluorescent which makes it a potential candidate for LED applications. Finally, the polymer is soluble in many different organic solvents with a strong absorption in the visible region which brings out the possible use of this material as an active layer in solar cells.

The monomer is designed to provide a strong donor-acceptor interaction and high solubility for the corresponding polymer. For that matter, benzotriazole was alkylated with dodecyl bromide to enhance the solubility. The alkylated benzotriazole was brominated in the presence of hydrobromic acid. Thiophene was stanylated in the presence of n-BuLi and tributyltin chloride. The final coupling reaction was achieved by Stille coupling reaction using $Pd(PPh_3)_2Cl_2$ as the catalyst. Utilizing this process, variable donor units can be coupled with benzotriazole derivatives in order to achieve donor-acceptor (D-A-D) type materials those may show similar or better results. Different derivatives are shown below.

D—A—D

Formula I

A-R1: $C_nH_{2n-1}$
A-R2: $C_nH_{2n}X$  X: F, Br, Cl, I, OH, $SO_3H$, $SO_3Na$, OTs
A-R3: O—R  R: $C_nH_{2n+1}$, $(C_nH_{2n}—O)_m$

A-R4

A-R5

A-R6

D1: 
D1R1: H
D1R2: $C_nH_{2n+1}$
D1R3: $C_nH_{2n}X$
X: F, Br, Cl, I, OH, $SO_3H$, $SO_3Na$, OTs, COH, COOH, O—$C_nH_{2n+1}$

D—A—D

Formula I

D2: 
D2R1: H
D2R2: $C_nH_{2n+1}$
D2R3: $C_nH_{2n}X$
X: F, Br, Cl, I, OH, $SO_3H$, $SO_3Na$, OTs, COH, COOH, O—$C_nH_{2n+1}$

D3: 
D3R1: H
D3R2: $C_nH_{2n+1}$
D3R3: $C_nH_{2n}X$
X: F, Br, Cl, I, OH, $SO_3H$, $SO_3Na$, OTs, COH, COOH, O—$C_nH_{2n+1}$

D4: 
D4R1: H
D4R2: $C_nH_{2n+1}$
D4R3: $C_nH_{2n}X$
X: F, Br, Cl, I, OH, $SO_3H$, $SO_3Na$, OTs, COH, COOH, O—$C_nH_{2n+1}$

D5: 
D5R1: H
D5R2: $C_nH_{2n+1}$
D5R3: $C_nH_{2n}X$
X: F, Br, Cl, I, OH, $SO_3H$, $SO_3Na$, OTs, COH, COOH, O—$C_nH_{2n+1}$

D6: 
D6R1: H
D6R2: $C_nH_{2n+1}$
D6R3: $C_nH_{2n}X$
X: F, Br, Cl, I, OH, $SO_3H$, $SO_3Na$, OTs, COH, COOH, O—$C_nH_{2n+1}$

The symbols used in the definition of derivatives of the conducting polymer are explained below:
A: Benzotriazole
D: thiophene (D1) or R-ethylenedioxythiophene (D2) or R-selenophene (D3) or ethylenedioxyselenophene (D4) or pyrrole (D5) or ethylenedioxypyrrole (D6)
R in A; $C_nH_{2n+1}$ (R1), $C_nH_{2n}X$ (R2), O—R(R3) where R is either $C_nH_{2n+1}$ or $(C_nH_{2n}—O)_m$, phenyl (R4), N-alkyl carbazole (R5), N-alkyl pyrrole (R6);
R in D; H(R1), $C_nH_{2n+1}$ (R2), $CnH_{2n}X$ (R3)
X in A-R2; F, Br, Cl, I, OH, $SO_3H$, $SO_3Na$, OTs;
X in D1R3, D2R3, D3R3, D4R3, D5R3 and D6R3; F, Br, Cl, I, OH, $SO_3H$, $SO_3Na$, OTs, COH, COOH, O—$C_nH_{2n+1}$.
where n is zero or greater than zero,
m is zero or greater than zero.
AR1-D2R1 and AR1-D3R1 was synthesized previously.[18a, 18b] All others can be synthesized by the process of this invention.

Figure 1:
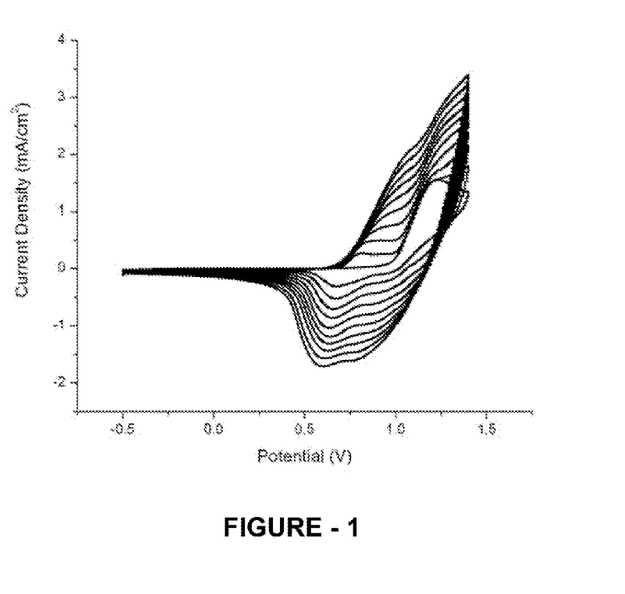
FIG. 1: Repeated potential-scan electropolymerization of TBT in 0.1 M ACN/TBAPF$_6$ solvent-electrolyte system at a scan rate of 100 mVs$^{-1}$ on ITO electrode.
Figure 6:
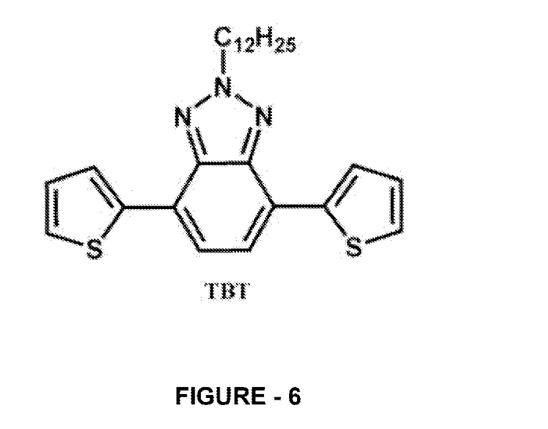
FIG. 6: Chemical structure of monomer, TBT.
Figure 7:
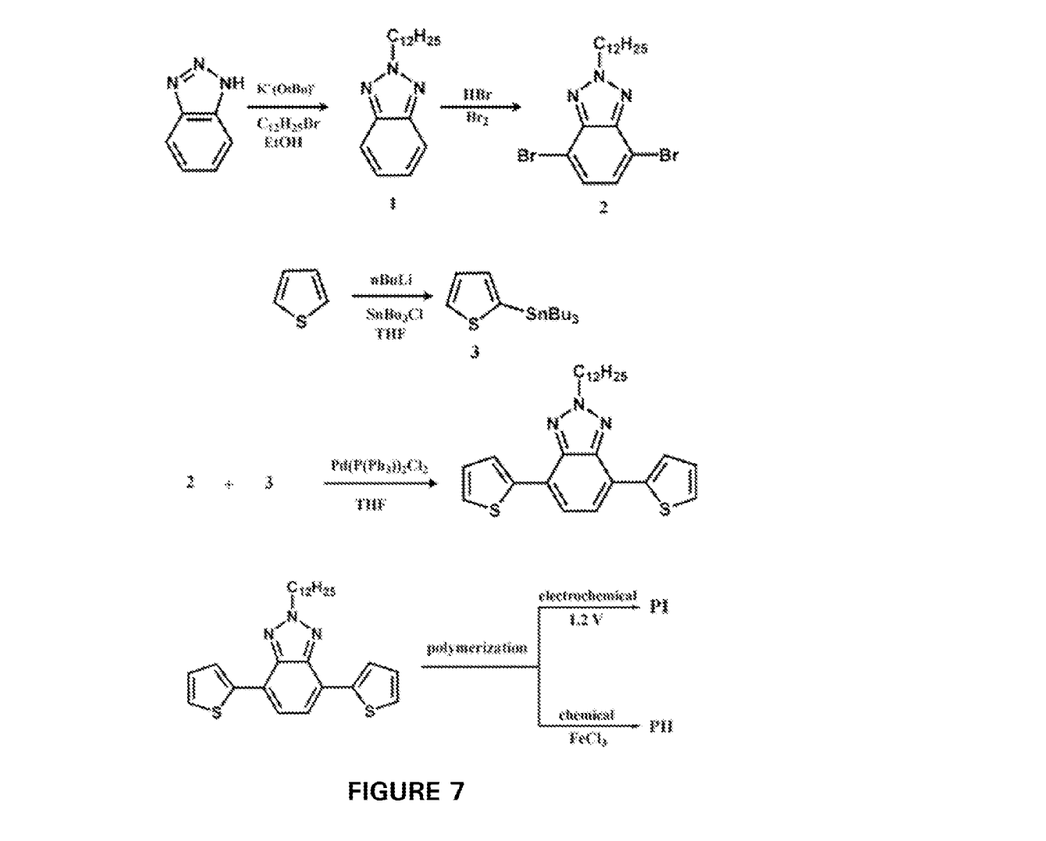
Figure 8:
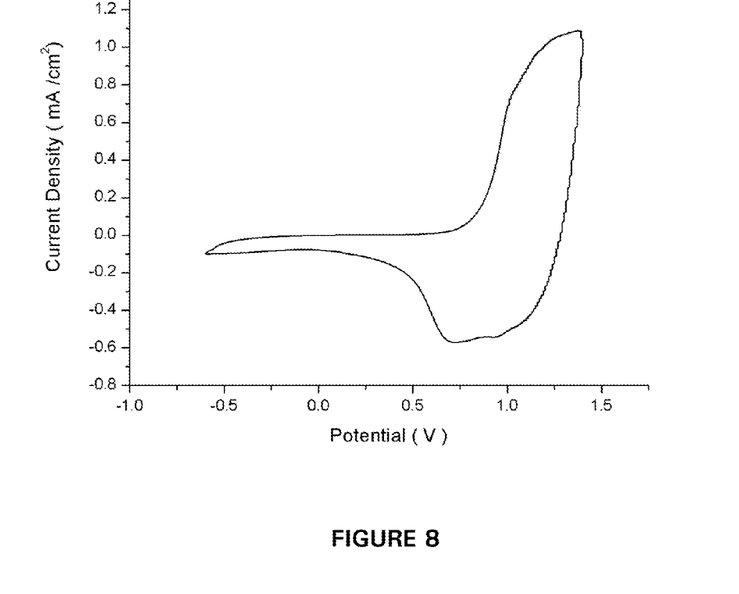
Figure 9:
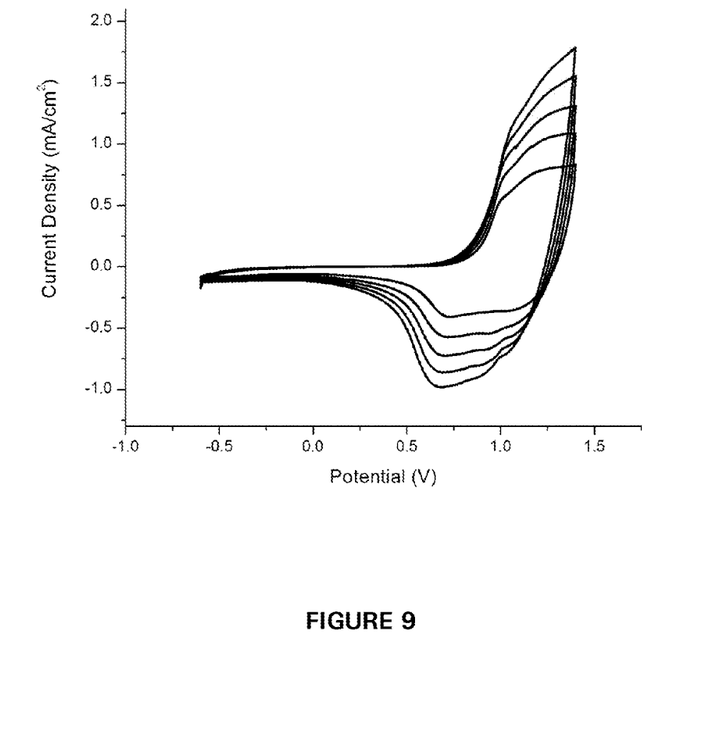
Figure 10:
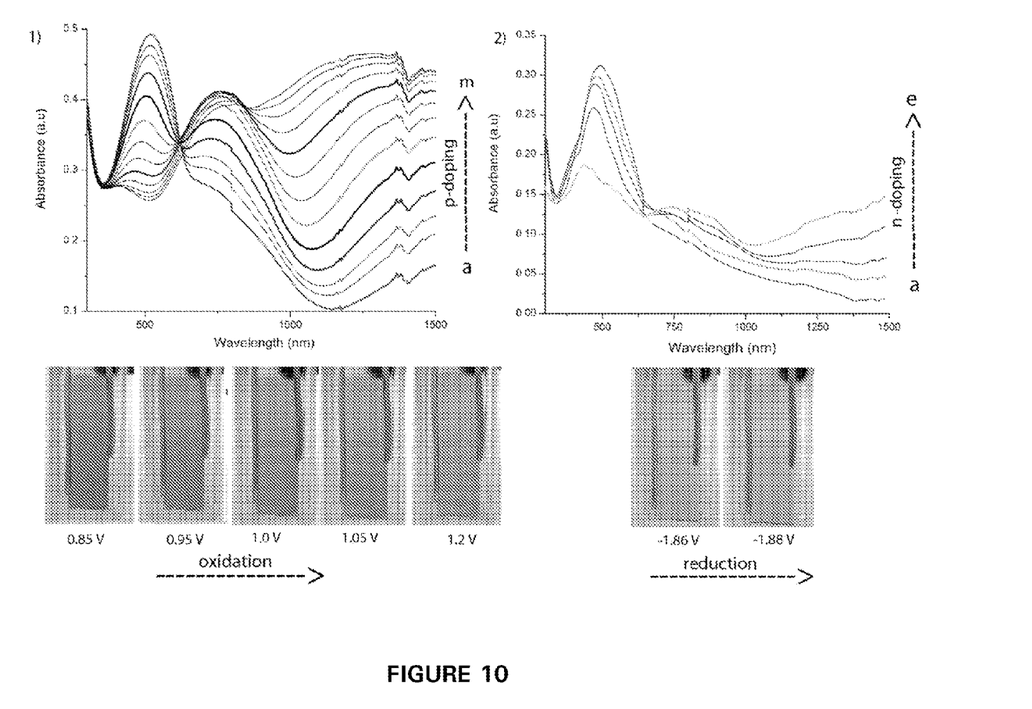
Figure 11:
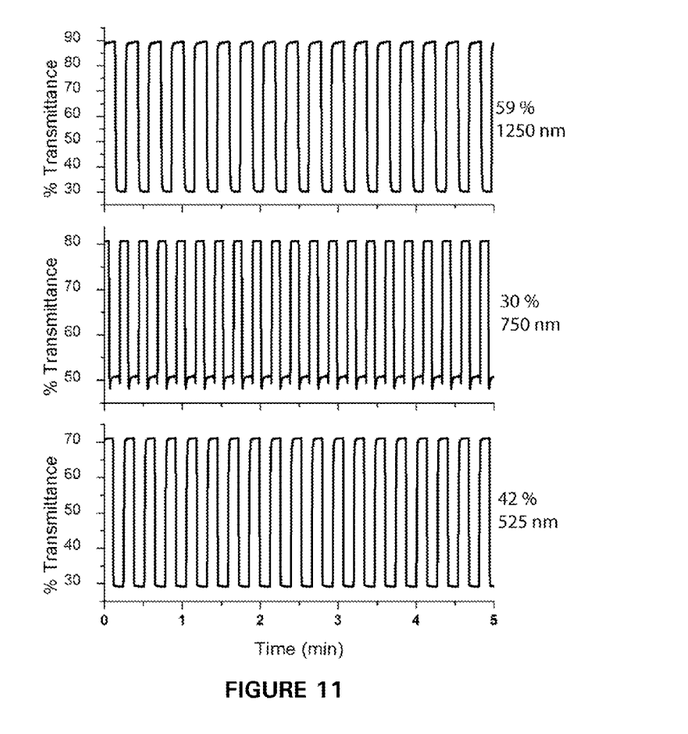

The homopolymer of 2-dodecyl-4,7-di(thiophen-2-yl)-2H-benzo[d][1,2,3]triazole (TBT: AR1-D1R1) (FIG. 6) was synthesized both electrochemically (PI) and chemically (PII), PI was successfully produced by oxidative ejectropolymerization from an acetonitrile (ACN) solution containing $10^{-2}$ M TBT and 0.1 M tetrabutylammonium hexafluorophosphate (TBAPF$_6$) on indium tin oxide (ITO) coated glass slides. The monomer oxidation occurs at 1.2 V vs. Ag wire pseudo reference electrode (0.35 V vs. SCE). A reversible redox couple evolved a potentials 1.0 V and 0.6 V as the electroactive PI deposits on ITO surface (FIG. 1).

Figure 2:
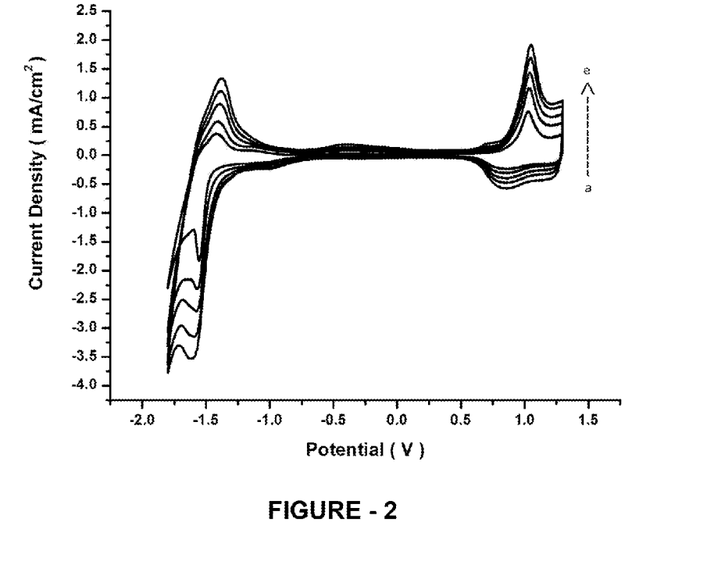
FIG. 2: Scan rate dependence of PI film in ACN/TBAPF$_6$ at: (a) 100, (b) 150, (c) 200, (d) 250 and (e) 300 mVs$^{-1}$

The unique n-doping property for conjugated polymer systems was clearly observed by cyclic voltammetry (CV) for N with a reversible redox couple at −1.4 V (ox.) and −1.6 V (red.) versus Ag wire reference electrode. As seen from FIG. 2 the scan rate dependence of PI was investigated by CV and a true linear relation was observed between the peak current and the scan rate, which indicates the presence of a well adhered electroactive film with a non-diffusion limited redox process.[8] In addition even at high scan rates, oxidation and reduction processes are still reversible.

Stability of the polymer film (PI) was investigated on an ITO glass slide where the polymer was subjected to potential cycling between its neutral and oxidized states in propylene carbonate (PC) and lithium perchlorate (LiClO$_4$) solvent-electrolyte couple. After 1000 cycles, no considerable change in the optical density and the injected/ejected charge per unit area were observed. PI revealed high stability without any charge loss after repeated cycles. (FIG. S-6)

Figure 3:
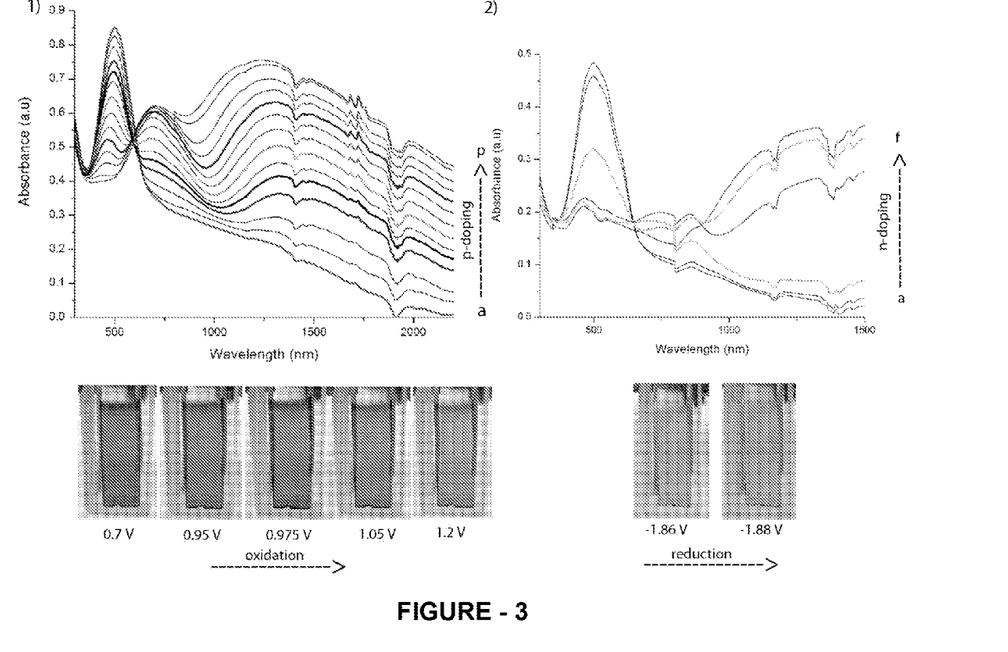
FIG. 3: Electronic absorption spectra and the colors of PI film on ITO coated glass slide in monomer free 0.1M TBAPF$_6$/ACN electrolyte-solvent couple at applied potentials (V). (1) p-doping; (a) 0.700, (b) 0.800, (c) 0.850, (d) 0.900, (e) 0.925, (f) 0.950, (g) 0.975, (h) 1.00, (1) 1.05, a) 1.10, (k) 1.15, (I) 1.20, (m) 1.25, (n) 1.30, (o) 1.35 and (p) 1.40 V. (2) n-doping; (a) −1.84, (b) −1.85, (c) 1.86, (d) −1.87, (e) (f)−1.89 V.

The optoelectrochemistry of the polymer revealed an absorption maximum at 503 nm corresponding to the n-n' transition of the polymer and the band gap of the polymer was calculated to be 1.65 eV from this transition, (FIG. 3)

The polymer is deep red in its neutral state. Upon oxidation the absorption at 503 nm depletes and a new absorption band forms at 700 nm due to the formation of polaron band. Since the polaron band of the polymer is still in the visible region during the depletion of n-n*, the polymer reveals several distinct colors. Upon oxidation, the deep red color of the polymer turns into brown. Further oxidation results in black which is a rare and significant property for an electrochromic polymer. Having black color in any state makes the polymer a significant candidate for smart window applications.[20] A green color was observed as the doping proceeds. Generation of a green color in a polymeric system is remarkable since one should have two simultaneous absorptions at around 400 and 700 nm.[21, 15] As the potential is further increased the polymer turns into a deep blue color. One remarkable point is that incremental increases in potential turn out to be enough to have all above mentioned colors. The corresponding L a b values for all colors can be found in the supporting information (Table S-1.).

The unique property of PT should be clearly addressed at this point. The polymer reveals all three primary additive colors. This points out that with proper engineering and modification in the polymer structure, PT can be realized as a single component electrochromic display device.

The reduction of a polymer does not necessarily mean an n-doping process is taking place. To identify a true n type doping one should observe considerable structural and optical differences after introducing charge carries to the conjugated system.[22] Hence, to clearly demonstrate the presence of n-type doping process, both the electrochemistry of the reduced state and the spectral changes upon reduction should be investigated. A similar study that can easily be performed for p-doping process, in theory, should also be repeated for n-doping process. However, this unique property for conducting polymers was observed in only handful of studies in literature.[14]

In these studies, the optoelectrochemistry of the polymer film in n-doping can only been observed in inert atmosphere conditions; only few data were acquired under ambient conditions.[23, 15b] During the investigation of PI it was striking to notice that six data were collected in the optoelectrochemistry studies, clearly showing that a true n-doping process occurs and it also reveals that the polymer shows a tremendous stability in its n-doped state. When the polymer is reduced (n-doped), it reveals a light blue color and upon further successive reduction, the polymer film becomes almost transparent, a highly desired property for these materials in electrochromic device applications. Properties observed for the absorption spectrum in polymer's neutral state are much like that of polyhexylthiophene,[24] one of the most promising materials for polymeric solar cell applications.[25] Performance of PI in a solar cell device will be investigated in due course, since the ease of synthesis, high solubility in organic solvents and strong absorption in the visible region are highly sought properties.

Figure 4:
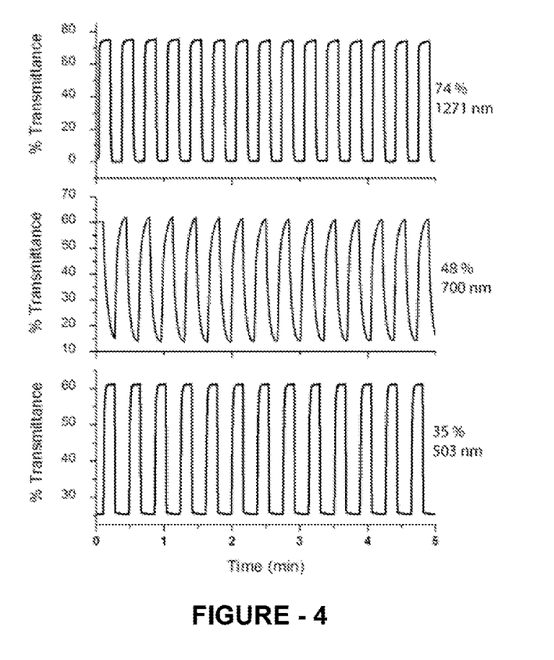
FIG. 4: Electrochromic switching: optical absorbance change monitored at 503, 700 and 1271 nm for PI in 0.1 M TBAPF$_6$/ACN while switching between its fully reduced and oxidized states.

Kinetic studies were performed to investigate the optical contrast and switching time of the polymer both in the visible and NIR regions. (FIG. 4) The polymer film coated on ITO glass showed a 37% optical contrast at 503 nm when switched between its reduced and oxidized states. The optical contrast value is significantly higher than the optical contrast of polythiophene. The switching time of the polymer was calculated as 2 s. This time period is the duration for switching among five different colors and hence, does not refer to switching between two colors which is the usual way of reporting switching times. That is to say, the reported time (2 s) cannot be considered as a long one since it stands for the time required for five color transitions. Thus, it is reasonable to claim that the switching time between any two colors is about 0.5 s on the average. The optical contrast of the polymer in NIR region was found to be 74% with a switching time of 0.6 s which makes this polymer also a powerful candidate for NIR electrochromic applications. The NIR applicable materials are of particular interest since they are used for optical data transmission and the NIR dyes.[26]

Chemical polymerization of the monomer has been achieved by simple FeCl$_3$ polymerization (see SI. for details). The resulting polymer (PII) was purified, dissolved in chloroform and spray coated on ITO electrodes. CV (FIG. SI-1), scan rate dependence (FIG. SI-2), spectroelectrochemistry (FIG. SI-3) and kinetic studies (FIG. SI-4) were performed for the spray coated PII film, and very similar results compare to PI were formed. This implies that since the material can be synthesized in large scale, the polymer is well suited for all industrial applications that the material showed unique properties for.

Figure 5:
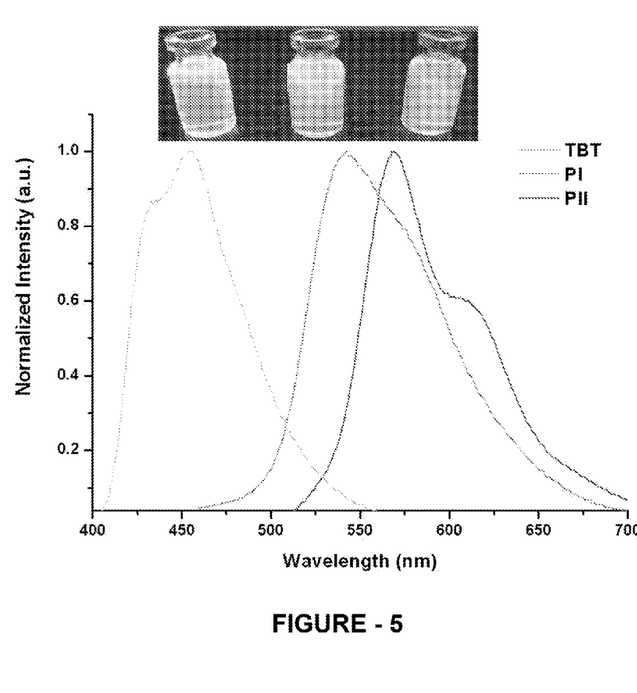
FIG. 5: Emission spectra of TBT, PI and PII solutions in chloroform and emission photographs when solutions were exposed to a standard UV lamp (366 nm).

Fluorescence spectra obtained for TBT, PI and PII are depicted in FIG. 5. The solutions of TBT, PI and PII in chloroform were excited at 380 nm, 447 nm, and 496 nm at around their absorption maxima and maximum emission wavelengths of 454 nm, 542 nm and 569 nm were obtained respectively. Due to the extension of repeating unit in polymer chain, which was estimated from molecular weight determination (Table S-2), quenching is increasing. Qualitative comparison suggests that the red shifted emission intensities are decreasing with increasing repeating unit. Difference in molecular weight between polymers leads to a longer absorption maximum wavelength for PII than that of PI (FIG. S-5). Thus, PI is orange-red in solution whereas PII is red.

As previously reported by Sonmez et. al., polymeric electrochromes can be used in memory device applications due to their small power requirements for optical changes and abilities to have different tones of colors in different oxidation states.[27] Color variation is the major parameter that can enhance the capacity of such devices. According to the color mixing theory, it is possible to obtain all colors by three primary additive colors, red, green and blue.[28] Up to date, this was possible via using different polymers which have a transmissive state to obtain these colors.[15,29,30] Now, both PI and PII make it possible to obtain all colors required for commercial electrochromic applications of conjugated polymers via using the same polymer in its different oxidation states, with the advantage of working in a very small potential range. This makes them outstanding candidates for data storage applications.

Supporting Information:

EXPERIMENTAL

General:

All chemicals were purchased from Aldrich except THF which was purchased from Acros. Tributyl(thiophene-2-yl) stannane was synthesized according to a previously described method. [S. S. Zhu, T. M. Swager, *J. Am. Chem. Soc.* 1997, 119, 12568-12577.] All reactions were carried out under argon atmosphere unless otherwise mentioned. For all electrochemical studies a Voltalab 50 potentiostat was used. Electropolymerization was performed in a three-electrode cell consisting of an Indium Tin Oxide doped glass slide (ITO) as the working electrode, platinum wire as the counter electrode, and Ag wire as the reference electrode. $^1$H and $^{13}$C NMR spectra were recorded in CDCl$_3$ on Bruker Spectrospin Avance DPX-400 Spectrometer. Chemical shifts were given in ppm downfield from tetramethylsilane. Varian Cary 5000 UV-Vis spectrophotometer was used to perform the spectroelectrochemical studies of the polymer. Fluorescence measurements were conducted using a Varian Eclipse spectrofluorometer. Column chromatography of all products was performed using Merck Silica Gel 60 (particle size: 0.040-0.063 mm, 230-400 mesh ASTM). Reactions were monitored by thin layer chromatography using fluorescent coated aluminum sheets. Solvents used for spectroscopy measurements were spectrophotometric grade. Colorimetry measurements were done via Minolta CS-100 Spectrophotometer. Mass analysis was carried out on a Bruker time of flight (TOF) mass spectrometer with an electron impact ionization source. Average molecular weight was determined by gel permeation chromatography (GPC) using a Polymer Laboratories GPC 220.

Synthesis of 2-dodecylbenzotriazol

Synthesis of 2-dodecylbenzotriazole was performed according to methodology described in literature. [A. Tanimoto, T. Yamamoto, Macromolecules 2006, 39, 3546. b) A. Balan, G. Gunbas, A. Durmus, L. Toppare, *Chem. Mater.* 2008, 20, 7510-7513.]1,2,3-Benzotriazole (5.0 g, 42 mmol), potassium tert-butoxide (5.0 g, 44 mmol) and bromododecane (12.2 g, 49 mmol) were dissolved in methanol (50 mL). The reaction mixture was refluxed for 12 h and monitored by TLC. After removal of the solvent by evaporation, the residue was dissolved in CHCl$_3$ and extracted with water. The organic extract was dried over MgSO$_4$ and the solvent was evaporated under reduced pressure. Column chromatography on silica gel was performed to obtain 2-dodecylbenzotriazole as a colorless oil (3.7 g, 31%). $^1$H NMR (400 MHz, CDCl$_3$, δ): 7.76 (m, 2H), 7.26 (m, 2H), 4.62 (t, J=7.1 Hz 2H), 2.12 (m, 2H), 1.25-1.15 (m, 18H), 0.78 (t, J=6.0 Hz, 3H); $^{13}$C NMR (100 MHz, CDCl$_3$, δ): 144.3, 126.1, 117.9, 56.6, 31.8, 30.0, 29.5, 29.4, 29.4, 29.3, 29.3, 29.0, 26.5, 22.6, 14.0.

Synthesis of 4,7-dibromo-2-dodecylbenzotriazole

[A. Tanimoto, T. Yamamoto, Macromolecules 2006, 39, 3546. b) A. Balan, G. Gunbas, A. Durmus, L. Toppare, *Chem. Mater.* 2008, 20, 7510-7513.]

2-Dodecylbenzotriazole (3.7 g, 13.1 mmol) and an aqueous HBr solution (5.8 M, 15 ml) were added to a flask, and the mixture was stirred for 1 h at 100° C. Bromine (5.9 g, 36 mmol) was added, and the mixture was stirred for 12 h at 135° C. After cooling the mixture to room temperature, an aqueous solution of NaHCO$_3$ was added and the product was extracted with CHCl$_3$. The organic layer was dried over MgSO$_4$ and the solvent was evaporated under reduced pressure. With column chromatography, 4,7-dibromo-2-dodecylbenzotriazole was obtained as light yellow oil (4.3 g, 75%). $^1$H NMR (400 MHz, CDCl$_3$, δ): 7.36 (s, 2H), 4.60 (t, J=7.0 Hz, 2H), 2.10 (m, 2H), 1.38-1.12 (m, 18H), 0.80 (t, J=6.9 Hz, 3H). $^{13}$CNMR (100 MHz, CDCl$_3$, δ): 143.7, 129.4, 109.9, 57.4, 31.8, 30.1, 29.5, 29.5, 29.4, 29.4, 29.3, 28.9, 26.4, 22.6, 14.0.

Synthesis of 2-dodecyl-4,7-di(thiophen-2-yl)-2H-benzo[d][1,2,3]triazole (TBT)

4,7-Dibromo-2-dodecylbenzotriazole (100 mg, 0.224 mmol), and tributyl(thiophen-2-yl)stannane were dissolved in anhydrous THF (100 ml) and dichlorobis (triphenylphosphine)-palladium(II) (50 mg, 0.045 mmol) was added at room temperature. The mixture was refluxed for 12 hours under argon atmosphere. Solvent was evaporated under vacuum and the crude product was purified by column chromatography on silica gel to obtain 75 mg (74%) TBT. $^1$H NMR (400 MHz, CDCl$_3$, δ): 8.01 (d, J=5.6 Hz, 2H), 7.52 (s, 2H), 7.28 (d, J=6.0 Hz, 2H), 7.09 (t, J$_A$=8.8 Hz, J$_B$=4.8, 2H), 4.60 (t, J=7.0 Hz, 2H), 2.10 (m, 2H), 1.38-1.15 (m, 18H), 0.80 (t, J=6.9 Hz, 3H); $^{13}$C NMR (100 MHz, DMSO-d$_6$, δ): 142.4, 140.2, 128.4, 127.3, 125.8, 123.9, 123.0, 57.1, 32.2, 30.3, 29.9, 29.8, 29.7, 29.6, 29.5, 29.3, 26.9, 22.9, 14.4. MS (m/z): 451 [M+]

Chemical Polymerization of TBT (PII):

For the chemical polymerization of the donor-acceptor-donor (DAD) structured compounds of Formula I, following steps are exercised:

First of all, (DAD) structured compound of Formula I was dissolved in an organic solvent. Then FeCl$_3$ were suspended in an organic solvent and slowly added to the DAD solution. The mixture is stirred and added into an alcohol. The precipitate was dissolved in an organic solvent and extracted with water or brine several times. Organic phase was dried with a drying agent and evaporated. Then the residue was dissolved in an organic solvent and the mixture was stirred with a reducing agent in order to de-dope polymer completely. The organic solvent was evaporated under reduced pressure. The organic solvent was added to the residue and organic phase was extracted with water or brine. Combined organic phases were evaporated and the residue was stirred in acetone or alcohol to remove unreacted monomers. In the final step, the polymer was filtered and dried under vacuum.

For the above mentioned chemical polymerization of the donor-acceptor-donor (DAD) structured compounds of Formula I, organic solvent is selected from, chloroform, dichloromethane, nitromethane, chlorobenzene, dichlorobenzene, THF, DMF, DMSO, diethyl ether and reducing agent is selected from, hydrazine or hydrated hydrazine, hydroxy bases, metals.

Chemical polymer is also synthesized via coupling based polymerization such as Stille coupling or Suzuki coupling.

For the preferred chemical polymerization of the donor-acceptor-donor (DAD) structured compounds of Formula I, following steps are exercised:

100 mg TBT (DAD) was dissolved in 10 mL of $CHCl_3$ under argon atmosphere. $FeCl_3$ (142 mg) were suspended in 10 mL of nitromethane and slowly added to the monomer solution. Yellow solution slowly turned to deep green and finally deep blue. The mixture was stirred for 4 h and then added into 200 mL methanol. The precipitate was dissolved in $CHCl_3$ and extracted with water several times. The organic phase was dried with magnesium sulfate and evaporated. Residue was dissolved in 50 mL THF and 50 mL hydrazine monohydrate was added. In order to de-dope the polymer completely, mixture was stirred for 12 h and during this period solution turned to dark red. THF was evaporated under reduced pressure. Chloroform was added to the residue and the organic phase was extracted several times with water. Combined organic phases were evaporated and the residue was stirred in acetone to remove unreacted monomers. The polymer was filtered and dried under vacuum to give PII as a dark-red solid. $^1$H NMR (400 MHz, $CDCl_3$, δ): 7.50 (benzotriazole), 7.2 (thiophene), 7.0 (thiophene), 4.6 (N—$CH_2$), 1.5-0.8 (pendant alkyl chain).

TABLE S-1

L, a, b values for distinctive colors of PI at different oxidation states.

| Colors | L | a | b |
|---|---|---|---|
| Red (p) | 43.98 | 58.99 | 16.53 |
| Brown (p) | 55.59 | 17.26 | 16.67 |
| Black (p) | 67.32 | 0.148 | 1.72 |
| Green (p) | 69.26 | −34.14 | 31.29 |
| Blue (p) | 64.71 | −6.1 | −38.72 |
| Blue (n) | 77.48 | −7.64 | −21.21 |
| Transmissive (n) | 86.67 | 2.78 | −16.94 |

TABLE S-2

GPC Molecular weight determination for PI and PII (in THF).

| Polymer | $M_n$ (g/mol) | $M_w$ (g/mol) | PDI | Avg. No. Rep. Un. |
|---|---|---|---|---|
| PI | 13000 | 23400 | 1.80 | 28 |
| PII | 44000 | 239600 | 5.44 | 97 |

As a conclusion, both PI and PII combine unique properties in a single material and represent a very promising multifunctional electrochromic polymer. The material reveals multichromism with six distinct colors and high stability. The polymers have shown to be both p- and n-dopable. The spectroelectrochemistry of the n-doped state could be studied at ambient conditions, which signifies it as one of the most stable n-doped polymers in the literature. The polymers revealed very good optical contrast and switching times compared to the homopolymer of the donor unit (polythiophene). The polymers reveal black color upon oxidation, and are highly transparent in completely reduced state implying that they can be excellent candidates for highly efficient smart windows. PI also revealed 75% optical contrast in the NIR region which makes it a significant candidate for NIR electrochromic device applications. PII has shown identical properties with PI which is important for large scale commercial applications. One of the most significant properties was to be able to observe all three primary colors in a single material. The saturation of the colors can be improved with small modifications in the polymer backbone and with intelligent engineering hence; a single component electrochromic display device can be realized. In addition, the polymer reveals highly efficient emission upon irradiation (LED applications). Strong absorption in the visible region makes this polymer a promising candidate for solar cell applications. We believe that PTBT will be a multipurpose material that will receive a great deal of the attention from industry.

The invention claimed is:

1. A conducting polymer, consisting of repeating unit which is selected from the compounds of general Formula I Formula I in which $r_1$ is selected from group consisting of $C_nH_{2n+1}$, $C_nH_{2n}x$ wherein x is F, Br, Cl, I, OH, $SO_3H$, $SO_3Na$, OTs, $OC_nH_{2n+1}$, $O(C_nH_{2n}O)_m$, phenyl, N-alkyl carbazole, and N-alkyl pyrrole;

d is selected from the following group where $r_2$ is selected from group consisting of hydrogen, $C_nH_{2n+1}$, $C_nH_{2n}x$ wherein x is F, Br, Cl, I, OH, $SO_3H$, $SO_3Na$, OTs COH, COOH, and $OC_nH_{2n+1}$; which shows red, green, blue colors as well as black and transparent and is both p and n type dopable and soluble in chloroform, dichloromethane, nitromethane, chlorobenzene, dichlorobenzene, tetrahydrofuran, dimethylformamide, dimethylsulfoxide or diethyl ether, wherein n is an integer ≧0 and m is an integer >0.

* * * * *